(12) United States Patent
Dhingra

(10) Patent No.: US 6,524,551 B2
(45) Date of Patent: Feb. 25, 2003

(54) SYNTHESIS OF MCM-58

(75) Inventor: Sandeep S. Dhingra, Midland, MI (US)

(73) Assignee: ExxonMobil Oil Corporation, Fairfax, VA (US)

( * ) Notice: Subject to any disclaimer, the term of this patent is extended or adjusted under 35 U.S.C. 154(b) by 0 days.

(21) Appl. No.: 10/057,322

(22) Filed: Jan. 25, 2002

(65) Prior Publication Data

US 2002/0164284 A1 Nov. 7, 2002

Related U.S. Application Data

(60) Provisional application No. 60/264,365, filed on Jan. 26, 2001.

(51) Int. Cl.$^7$ ................................................ C01B 39/48
(52) U.S. Cl. ...................... 423/706; 423/709; 585/446; 585/467; 585/475; 585/739
(58) Field of Search ................................ 423/706, 709; 585/475, 446, 467, 739

(56) References Cited

U.S. PATENT DOCUMENTS

| 4,544,538 A | * | 10/1985 | Zones | ........................ 423/706 |
|---|---|---|---|---|
| 4,665,110 A | * | 5/1987 | Zones | ........................ 423/305 |
| 5,437,855 A | | 8/1995 | Valyocsik | .................... 423/706 |
| 5,441,721 A | | 8/1995 | Valyocsik | .................... 423/706 |
| 5,653,956 A | | 8/1997 | Zones | ........................ 423/706 |
| 5,785,947 A | * | 7/1998 | Zones et al. | ................. 423/705 |

FOREIGN PATENT DOCUMENTS

WO          98/29332          7/1998

* cited by examiner

*Primary Examiner*—David Sample

(57) ABSTRACT

This invention provides a process for the synthesis of MCM-58 using 1-(1-adamantyl)pyridinium cations as a directing agent. The resultant MCM-58 is useful in a variety of hydrocarbon conversion reactions including toluene disproportionation, transalkylation of aromatics, reaction of paraffins with aromatics, paraffin isomerization and alkylation of aromatics with olefins.

9 Claims, 2 Drawing Sheets

SYNTHESIS OF MCM-58

CROSS-REFERENCE TO RELATED APPLICATIONS

This application claims priority to application Serial No. 60/264,365, filed Jan. 26, 2001, which is hereby incorporated by reference.

BACKGROUND OF THE INVENTION

1. Field of the Invention

This invention relates to a process for the synthesis of the porous crystalline material MCM-58, to MCM-58 produced by said process, and to use of the resultant MCM-58 as a catalyst for organic compound, e.g. hydrocarbon compound, conversion.

2. Discussion of the Prior Art

MCM-58 and its conventional preparation in the presence of N-benzylquinuclidinium cations as the directing agent are taught by U.S. Pat. No. 5,437,855, the entire disclosure of which is incorporated herein by reference. MCM-58 has a distinctive X-ray diffraction pattern which distinguishes it from other known crystalline materials.

U.S. Pat. No. 5,441,721 discloses a method for the synthesis of MCM-58 from a reaction mixture comprising, as a directing agent, the novel cation, N-benzyltropanium cation which can be synthesized by reacting benzyl bromide with tropane.

U.S. Pat. No. 5,653,956 discloses a method for the synthesis of SSZ-42, which is isostructural with MCM-58, using an organic templating agent selected from the group consisting of N-benzyl-1,4-diazabicyclo[2.2.2]octane cations and N-benzyl-1-azabicyclo[2.2.2]octane cations. ITQ-4 is also isostructural with MCM-58 and, according to PCT Publication No. 98/29332, can be synthesized using N-benzylquinuclidinium cations or N-benzyl-1,4-diazabicyclo[2.2.2]octane cations as the directing agent.

The existing methods for the synthesis of MCM-58 and the related materials SSZ-42 and ITQ-4 suffer from the problem that they require the use of expensive materials as the directing agent. According to the present invention, it has now been found that MCM-58 can be synthesized using, as directing agent, 1-(1-adamantyl)pyridinium cations, which can be produced from, for example, the relatively inexpensive starting materials adamantyl bromide and pyridine.

It is to be appreciated that, although MCM-58 is normally synthesized as an aluminosilicate, the framework aluminum can be partially or completely replaced by other trivalent elements, such as boron, iron and/or gallium, and the framework silicon can be partially or completely replaced by other tetravalent elements such as germanium.

SUMMARY OF THE INVENTION

According to the invention, there is provided a process for synthesizing the porous, crystalline material MCM-58 which comprises the steps of:

(i) preparing a mixture capable of forming said material, said mixture comprising sources of alkali or alkaline earth metal (M), an oxide of trivalent element (X), an oxide of tetravalent element (Y), hydroxyl (OH⁻) ions, water and a 1-(1-adamantyl)pyridinium directing agent (R), wherein said mixture has a composition, in terms of mole ratios, within the following ranges:

$YO_2/X_2O_3 = 10–1000$
$H_2O/YO_2 = 5–100$
$OH^-/YO_2 = 0.005–1$
$M/YO_2 = 0.05–1$
$R/YO_2 = 0.01–0.4$ (ii) maintaining said mixture under sufficient conditions until crystals of said material are formed; and (iii) recovering said crystalline material from step (ii).

Preferably, said reaction mixture has a composition in terms of mole ratios within the following ranges:

$YO_2/X_2O_3 = 20–100$
$H_2O/YO_2 = 10–50$
$OH^-/YO_2 = 0.1–0.4$
$M/YO_2 = 0.1–0.4$
$R/YO_2 = 0.05–0.2$

DETAILED DESCRIPTION OF THE INVENTION

Figure 1:
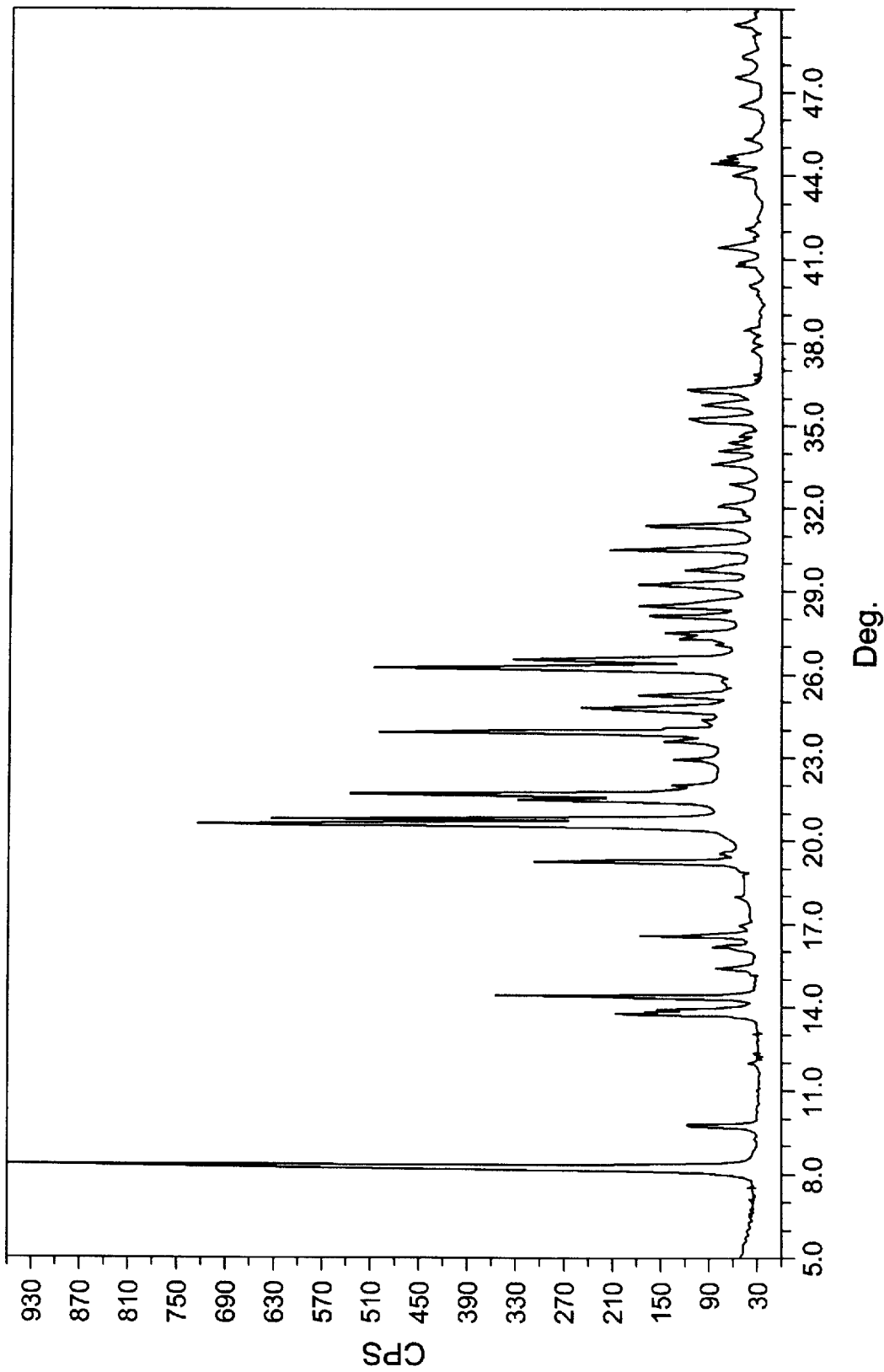
FIG. 1 shows the X-ray diffraction pattern of the as-synthesized product of Example 1.

In its as-synthesized form, the MCM-58 produced by the process of the invention has an X-ray diffraction pattern, characterized by the lines listed in Table 1 below:

TABLE 1

| D-spacing (Å) | Relative Intensity [100 × I/Io] |
| --- | --- |
| 10.89 + 0.30 | s-vs |
| 9.19 + 0.30 | vw |
| 6.55 + 0.29 | vw-w |
| 5.86 + 0.28 | vw-w |
| 5.57 + 0.27 | vw-w |
| 5.43 + 0.26 | vw-w |
| 4.68 + 0.25 | vw-m |
| 4.36 + 0.25 | w-vs |
| 4.17 + 0.23 | vw-m |
| 4.12 + 0.23 | vw-s |
| 3.78 + 0.20 | wv-s |
| 3.61 + 0.15 | vw-w |
| 3.54 + 0.15 | vw |
| 3.44 + 0.15 | vw-m |
| 3.37 + 0.15 | vw-m |
| 3.06 + 0.15 | vw-w |
| 2.84 + 0.15 | vw |
| 2.72 + 0.13 | vw |
| 2.66 + 0.12 | vw |
| 2.46 + 0.12 | vw |
| 2.17 + 0.10 | vw |

These X-ray diffraction data were collected with a Scintag diffraction system, equipped with a germanium solid state detector, using copper K-alpha radiation. The diffraction data were recorded by step-scanning at 0.02 degrees of two-theta, where theta is the Bragg angle, and a counting time of 10 seconds for each step. The interplanar spacings, d's were calculated in Angstrom units (A), and the relative intensities of the lines, I/I.sub.o is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (80–100), s=strong (60–80), m=medium (40–60), w=weak (20–40), and vw=very weak (0–20). It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, and thermal and/or hydrothermal history.

The crystalline material MCM-58 prepared hereby has a composition involving the molar relationship:

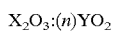

$$X_2O_3:(n)YO_2$$

wherein X is a trivalent element, such as aluminum, boron, iron, indium and/or gallium, preferably aluminum; Y is a tetravalent element, such as silicon, tin and/or germanium, preferably silicon; and n is from about 10 to about 1000 more usually from about 20 to about 100. In the as-synthesized form, the crystalline material prepared hereby has a formula, on an anhydrous basis and in terms of moles of oxides per n moles of $YO_2$, as follows:

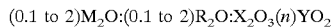

$$(0.1\ to\ 2)M_2O:(0.1\ to\ 2)R_2O:X_2O_3(n)YO_2$$

wherein M is an alkaline or alkaline earth metal and R is the 1-(1-adamantyl)pyridinium directing agent. The M and R components are associated with the material as a result of their presence during crystallization, and are easily removed by post-crystallization methods hereinafter more particularly described.

The process of the invention involves initially producing a synthesis mixture containing sources of alkali or alkaline earth metal (M) cations, an oxide of a trivalent element (X), normally alumina, an oxide of a tetravalent element (Y), normally silica, the directing agent 1-(1-adamantyl)pyridinium (R), normally present as the bromide, hydroxyl ions and water. The synthesis mixture has a composition, expressed in terms of mole ratios of oxides, as follows:

| Component | Useful | Preferred |
|---|---|---|
| $YO_2/X_2O_3$ | 10–1000 | 20–100 |
| $H_2O/YO_2$ | 5–100 | 10–50 |
| $OH^-/YO_2$ | 0.05–1 | 0.1–0.4 |
| $R/YO_2$ | 0.05–1 | 0.1–0.4 |
| | 0.01–0.4 | 0.05–0.2 |
| 0.01–0.4 | | |

The 1-(1-adamantyl)pyridinium bromide directing agent is commercially available from Aldrich Chemical Company but can also readily be synthesized by reaction of adamantyl bromide and pyridine. It has the following structural formula:

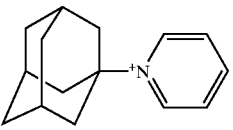

The synthesis method of the invention functions with or without added nucleating seeds. In a preferred embodiment, the reaction mixture contains 0.05–5 wt % nucleating seeds of MCM-58.

Crystallization is carried out under either stirred or static conditions at a temperature of 100 to 220° C., preferably 130 to 180° C., for 12 hours to 10 days and the resultant crystals are separated from the mother liquor and recovered.

MCM-58 synthesized by the process of the invention contains the organic material used as the directing agent and, prior to use as a catalyst or adsorbent, the as-synthesized material is normally treated to remove part or all of the organic constituent. This is conveniently effected by heating the as-synthesized material at a temperature of from about 250° C. to about 550° C. for from 1 hour to about 48 hours.

To the extent desired, the original sodium and/or potassium cations of the as-synthesized material can be replaced in accordance with techniques well known in the art, at least in part, by ion exchange with other cations. Preferred replacing cations include metal ions, hydrogen ions, hydrogen precursor, e.g., ammonium ions and mixtures thereof. Particularly preferred cations are those which tailor the catalytic activity for certain hydrocarbon conversion reactions. These include hydrogen, rare earth metals and metals of Groups IIA, IIIA, IVA, VA, IB, IIB, IIIB, IVB, VB, VIB, VIIB and VIII of the Periodic Table of the Elements.

The crystalline material of this invention, when employed either as an adsorbent or as a catalyst in an organic compound conversion process should be dehydrated, at least partially. This can be done by heating to a temperature in the range of 200° C. to about 370° C. in an atmosphere such as air or nitrogen, and at atmospheric, subatmospheric or superatmospheric pressures for between 30 minutes and 48 hours. Dehydration can also be performed at room temperature merely by placing the MCM-58 in a vacuum, but a longer time is required to obtain a sufficient amount of dehydration.

Synthetic MCM-58 crystals prepared in accordance herewith can be used either in the as-synthesized form, the hydrogen form or another univalent or multivalent cationic form. It can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such components can be exchanged into the composition, impregnated therein or physically intimately admixed therewith. Such components can be impregnated in or on to the MCM-58 such as, for example, by, in the case of platinum, treating the material with a platinum metal-containing ion. Suitable platinum compounds for this purpose include chloroplatinic acid, platinous chloride and various compounds containing the platinum amine complex. Combinations of metals and methods for their introduction can also be used.

When used as a catalyst, it may be desirable to incorporate the MCM-58 prepared hereby with another material resistant to the temperatures and other conditions employed in certain organic conversion processes. Such matrix materials include active and inactive materials and synthetic or naturally occurring zeolites as well as inorganic materials such as clays, silica and/or metal oxides, e.g. alumina, titania and/or zirconia. The latter may be either naturally occurring or in the form of gelatinous precipitates, sols or gels including mixtures of silica and metal oxides. Use of a material in conjunction with the MCM-58, i.e. combined therewith, which is active, may enhance the conversion and/or selectivity of the catalyst in certain organic conversion processes. Inactive materials suitably serve as diluents to control the amount of conversion in a given process so that products can be obtained economically and orderly without employing other means for controlling the rate or reaction. Frequently, crystalline catalytic materials have been incorporated into naturally occurring clays, e.g. bentonite and kaolin. These materials, i.e. clays, oxides, etc., function, in part, as binders for the catalyst. It is desirable to provide a catalyst having good crush strength because in a petroleum refinery the catalyst is often subjected to rough handling, which tends to break the catalyst down into powder-like materials which cause problems in processing.

Naturally occurring clays which can be composited with the hereby synthesized crystalline material include the montmorillonite and kaolin families which include the subbentonites, and the kaolins commonly known as Dixie, McNamee, Georgia and Florida clays, or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the present crystals can be composited with a porous matrix material such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. The matrix can be in the form of a cogel. A mixture of these components could also be used.

The relative proportions of finely divided crystalline material and matrix vary widely with the crystalline material content ranging from about 1 to about 90 percent by weight, and more usually in the range of about 2 to about 50 percent by weight of the composite.

Aluminosilicate MCM-58 produced by the process of the invention is useful as a catalyst in organic compound, and in particular hydrocarbon, conversion reactions where acid activity is important. Specific examples include:

1) toluene disproportionation, with reaction conditions including a temperature of about 200° C. to about 760° C., a pressure of about atmospheric to about 60 atmospheres, a weight hourly space velocity (WHSV) of about 0.1 hr$^{-1}$ to about 20 hr$^{-1}$, and a hydrogen/hydrocarbon mole ratio of 0 (no added hydrogen) to about 50, to provide disproportionation product, including p-xylene;
2) transalkylation of aromatics, in gas or liquid phase, with reaction conditions including a temperature of about 100° C. to about 500° C., a pressure of about 1 to about 200 atmospheres, and a WHSV of 1 hr$^{-1}$ to about 10,000 hr$^{-1}$;
3) reaction of paraffins with aromatics to form alkylaromatics and light gases with reaction conditions including a temperature of about 260° C. to about 375° C., a pressure of about 0 to about 1000 psig, a WHSV of about 0.5 hr$^{-1}$ to about 10 hr$^{-1}$, and a hydrogen/hydrocarbon mole ratio of 0 (no added hydrogen) to about 10;
4) paraffin isomerization to provide branched paraffins with reaction conditions including a temperature of about 200° C. to about 315° C., a pressure of about 100 to 1000 psig, a WHSV of about 0.5 hr$^{-1}$ to about 10 hr$^{-1}$, and a hydrogen/hydrocarbon mole ratio of about 0.5 to about 10; and
5) alkylation of aromatics with olefins with reaction conditions including a temperature of about 200° C. to about 500° C., a pressure of about 0 to 500 psig, a total WHSV of about 0.5 hr$^{-1}$ to about 50 hr$^{-1}$, a hydrogen/hydrocarbon mole ratio of 0 (no added hydrogen) to about 10, and an aromatic/olefin mole ratio of from 1 to about 50.

In order to more fully illustrate the nature of the invention and the manner of practicing same, the following example is presented.

EXAMPLE 1

Colloidal silica (30 wt %), Al(OH)$_3$ (aluminum hydroxide, solid), KOH (potassium hydroxide, 20 wt % solution), the organic template 1-(1-adamantyl)pyridinium bromide (solid) and distilled water were combined in the following ratio:

| | |
|---|---|
| Si/Al$_2$ | 40 |
| H$_2$O/Si | 30 |
| OH/Si | 0.25 |
| K$^+$/Si | 0.25 |
| 1-(1-Adamantyl)pyridinium$^+$ Br$^-$/Si | 0.10 |

Figure 2:
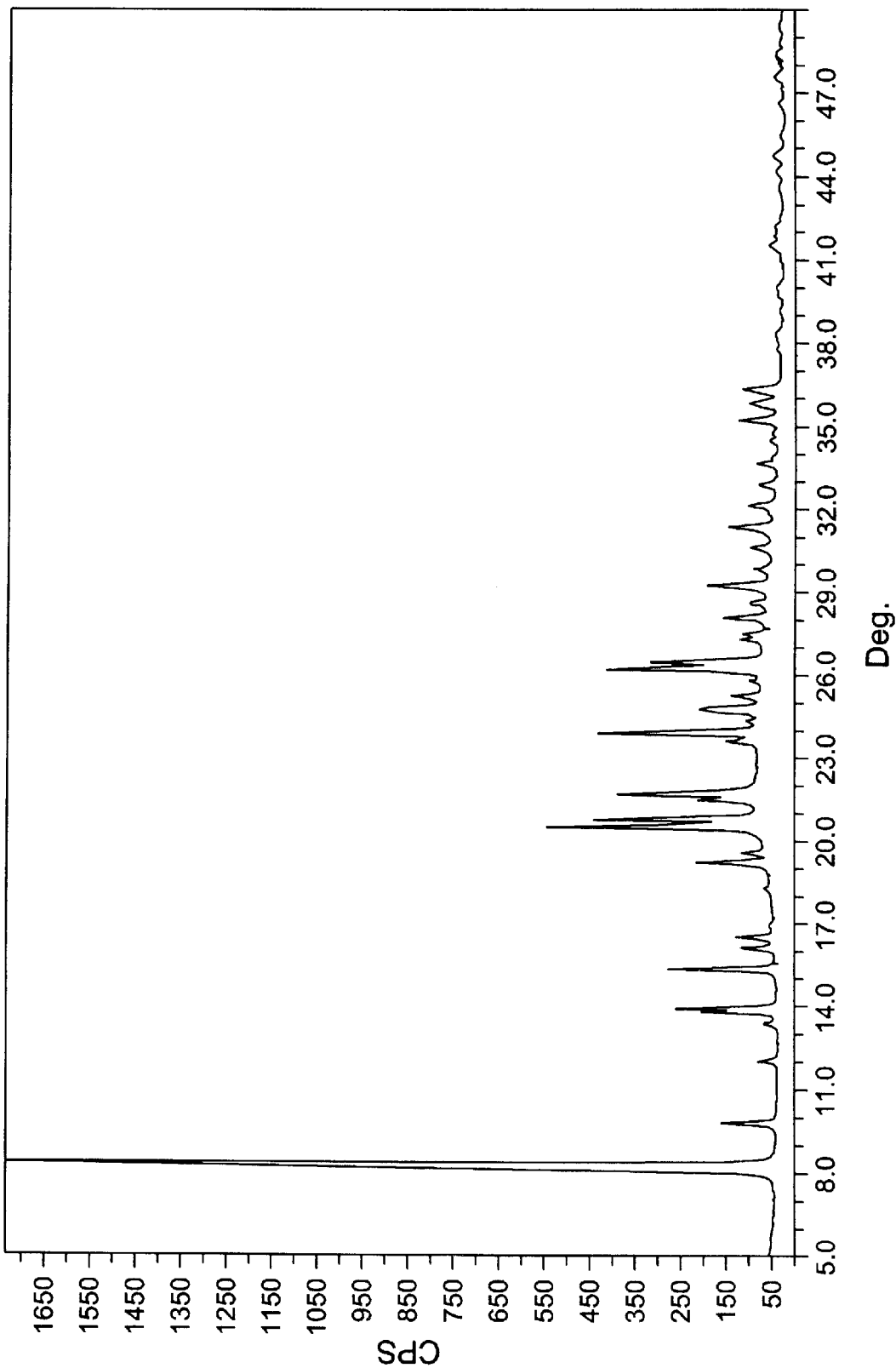
FIG. 2 shows the X-ray diffraction pattern of the calcined product of Example 2.

The combined mixture was added to an autoclave and heated to 160° C. for 150 hours stirred at 150 rpm. The product was then filtered and washed with water and dried overnight under an IR lamp. The solid was subsequently calcined under nitrogen at a temperature of 540° C. for 8 hours to yield MCM-58. The powder patterns of the as-synthesized and calcined MCM-58 are given in FIGS. 1 and 2, respectively.

The MCM-58 product had a silica/alumina molar ratio of about 40 with the Al environment being tetrahedral suggesting a high acid activity.

What is claimed is:

1. A process for synthesizing the crystalline material MCM-58 which comprises the steps of:
   (i) preparing a mixture capable of forming said material, said mixture comprising sources of alkali or alkaline earth metal (M), an oxide of trivalent element (X), an oxide of tetravalent element (Y), hydroxyl (OH$^-$) ions, water and a 1-(1-adamantyl)pyridinium directing agent (R), wherein said mixture has a composition, in terms of mole ratios, within the following ranges:
   YO$_2$/X$_2$O$_3$=10–1000
   H$_2$O/YO$_2$=5–100

$OH^-/YO_2 = 0.05–1$ $M/YO_2 = 0.05–1$ $R/YO_2 = 0.01–0.4$ (ii) maintaining said mixture under sufficient conditions until crystals of said material are formed; and (iii) recovering said crystalline material from step (ii).

2. The process of claim 1, wherein said reaction mixture has a composition in terms of mole ratios within the following ranges:

$YO_2/X_2O_3 = 20–100$ $H_2O/YO_2 = 10–50$ $OH^-/YO_2 = 0.1–0.4$ $M/YO_2 = 0.1–0.4$ $R/YO_2 = 0.05–0.2$

3. The process of claim 1, wherein said mixture further comprises seed crystals in sufficient amount to enhance synthesis of said crystalline material.

4. The process of claim 3, wherein said seed crystals have the structure of MCM-58.

5. The process of claim 1, wherein X is selected from the group consisting of aluminum, boron, iron, gallium, indium and mixtures thereof, and said Y is selected from the group consisting of silicon, germanium, tin and mixtures thereof.

6. The process of claim 1, wherein X comprises aluminum and Y comprises silicon.

7. MCM-58 synthesized by the process of claim 1.

8. A method for converting a feedstock comprising an organic compound to a conversion product which comprises contacting said feedstock at organic compound conversion conditions with a catalyst comprising an active form of the MCM-58 synthesized by the process of claim 1.

9. The method of claim 8 wherein the organic compound conversion is selected from the group consisting of toluene disproportionation, transalkylation of aromatics, reaction of paraffins with aromatics, paraffin isomerization and alkylation of aromatics with olefins.

* * * * *